United States Patent [19]

Narisada et al.

[11] 4,203,982
[45] May 20, 1980

[54] ARYLMALONAMIDOMETHOXYCEPH-ALOSPORINS

[75] Inventors: Masayuki Narisada, Ibaraki; Hiromu Matsumura, Ashiya; Wataru Nagata, Nishinomiya, all of Japan

[73] Assignee: Shionogi & Co., Ltd., Osaka, Japan

[21] Appl. No.: 819,931

[22] Filed: Jul. 28, 1977

[30] Foreign Application Priority Data

Aug. 10, 1976 [JP] Japan .................. 51-95732

[51] Int. Cl.$^2$ ............................. C07D 501/36
[52] U.S. Cl. ............................. 424/246; 544/21
[58] Field of Search .............. 544/27, 21; 424/246

[56] References Cited

U.S. PATENT DOCUMENTS

| | | | |
|---|---|---|---|
| 3,641,021 | 2/1972 | Ryan | 544/27 |
| 3,962,232 | 6/1976 | Koppel | 544/21 |
| 3,989,694 | 11/1976 | Berges | 544/27 |
| 3,993,758 | 11/1976 | Burton et al. | 544/27 |
| 4,041,029 | 8/1977 | Firestone et al. | 544/27 |
| 4,068,073 | 1/1978 | Berges | 544/27 |

FOREIGN PATENT DOCUMENTS

| | | | |
|---|---|---|---|
| 50-142592 | 4/1975 | Japan | 544/26 |
| 50-71693 | 6/1975 | Japan | 544/26 |
| 51-1489 | 1/1976 | Japan | 544/26 |

*Primary Examiner*—Nicholas S. Rizzo
*Attorney, Agent, or Firm*—Birch, Stewart, Kolasch and Birch

[57] ABSTRACT

Antibacterial 7$\beta$-arylmalonamido-7$\alpha$-methoxy-3-heterocyclic thiomethyl-3-cephem-4-carboxylic acids of the formula:

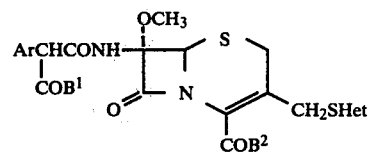

wherein Ar is a heterocyclic group or p-oxysubstituted phenyl; COB$^1$ and COB$^2$ are each a carboxy or protected carboxy group; and Het is an unsubstituted or substituted heterocyclic group. These compounds are prepared from, e.g., 7$\beta$-amino-7$\alpha$-methoxy-3-heterocyclic thiomethyl-3-cephem-4-carboxylic acid derivatives by acylation with arylmalonic acid or reactive derivatives thereof. They are useful as an active ingredient in antibacterial pharmaceutical preparations.

8 Claims, No Drawings

ARYLMALONAMIDOMETHOXYCEPHALOSPORINS

The invention relates to arylmalonamidomethoxycephalosporins. More specifically it relates to compounds of the following formula:

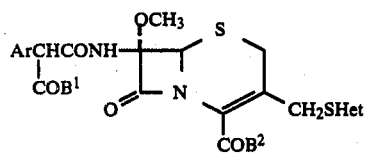

wherein Ar is furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, or a group of the formula:

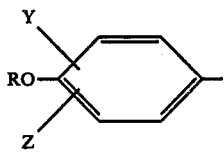

in which R is hydrogen, $C_1$ to $C_5$ alkanoyl (i.e. formyl, acetyl, propionyl, butyryl, isobutyryl, pentanoyl, isovaleryl, or pivaloyl), $C_7$ to $C_9$ aroyl (e.g. benzoyl, toluoyl, xyloyl, ethylbenzoyl, nitrobenzoyl, chlorobenzoyl), carbamoyl, thiocarbamoyl, N-trifluoroacetylcarbamoyl, N-trichloroethoxycarbonylcarbamoyl, N,N-di-$C_1$ to $C_3$ alkyl (i.e. methyl, ethyl, propyl, or isopropyl)-carbamoyl, $C_8$ to $C_{10}$ aralkoxycarbonyl as conventional hydroxy-protecting groups (e.g. carbobenzoxy, methylbenzyloxycarbonyl, methoxybenzyloxycarbonyl, nitrobenzyloxycarbonyl, or indanyloxycarbonyl), or $C_7$ to $C_9$ aralkyl as conventional hydroxyprotecting groups (e.g. benzyl, nitrobenzyl, chlorobenzyl, methylbenzyl, dimethylbenzyl, ethylbenzyl, methoxybenzyl, ethoxybenzyl, methoxybromobenzyl or ethoxynitrobenzyl); Y and Z each is hydrogen, hydroxy, halogen (e.g. fluorine, chlorine, or bromine), $C_1$ to $C_4$ alkoxy (i.e. methoxy, ethoxy, propoxy, isopropoxy, butoxy, isobutoxy, sec-butoxy, or t-butoxy), $C_1$ to $C_3$ alkyl (e.g. methyl, ethyl, propyl, or isopropyl), carbamoyloxy, or $C_7$ to $C_9$ aralkoxy as conventionally protected hydroxy groups (e.g. benzyloxy, nitrobenzyloxy, chlorobenzyloxy, methylbenzyloxy, dimethylbenzyloxy, ethylbenzyloxy, methoxybenzyloxy, ethoxybenzyloxy, methoxychlorobenzyloxy, or ethoxynitrobenzyloxy;

Het is furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, benzothienyl, pyridoxazolyl, benzothiazolyl, benzoxazolyl, or phenanthridyl, which may be substituted by optionally substituted $C_1$ to $C_4$ alkyl (e.g. methyl, ethyl, propyl, butyl, isobutyl, aminomethyl, acetylaminomethyl, propionylaminomethyl, methanesulfonylaminomethyl, hydroxymethyl, hydroxyethyl, formyloxymethyl, acetyloxymethyl, methoxyethyl, methoxymethyl, methylthiomethyl, or carboxymethyl or carboxyethyl optionally protected in the forms of esters or salts as is conventional in the chemistry of penicillins and cephalosporins as are explained for $COB^1$ and $COB^2$ infra); and $COB^1$ and $COB^2$ each is carboxy as is or protected carboxy conventional in the chemistry of penicillins and cephalosporins including the esters thereof (e.g. methyl, ethyl, isopropyl, butyl, t-butyl, pentyl, cyclopropylmethyl, cyclopropylethyl, monohydroxy-t-butyl, 2,2,2-trichloroethyl, chloromethyl, cyanomethyl, methanesulfonylethyl, acetylmethyl, acetoxymethyl, propionyloxymethyl, benzoyloxymethyl, methoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl, allyl, benzyl, phenethyl, tolylmethyl, dimethylbenzyl, nitrobenzyl, halobenzyl, methoxybenzyl, phthalidyl, p-hydroxy-di-t-butylbenzyl, diphenylmethyl, trityl, phenacyl, chlorophenacyl, bromophenacyl, nitrophenacyl, methylphenacyl trimethylsilyl, dimethylmethoxysilyl, trimethylstannyl, phenyl, naphthyl, tolyl, dimethylphenyl, nitrophenyl, methanesulfonylphenyl, chlorophenyl, pentachlorophenyl, indanyl, and pyridyl esters) or pharmacetically acceptable salts thereof (including sodium, potassium, (lithium, magnesium, paleium, acyloxycalcium, and aluminum salts), and salts useful for synthesis (e.g. procain, trimethylamine, triethylamine, diethylamine, and dicyclohexylamine salts). Each carboxy in the molecule can be free or protected by the same or different groups.

Important groups for Ar are thienyl, hydroxyphenyl, dihydroxyphenyl, trihydroxyphenyl, halohydroxyphenyl, dihalohydroxyphenyl, acetoxyphenyl, butyryloxyphenyl, methoxy-4-hydroxyphenyl, methyl-4-benzoyloxyphenyl, methoxy-4-acetoxyphenyl, carbamoyloxyphenyl, methoxy-4-carbamoyloxyphenyl, dicarbamoyloxyphenyl, N,N-dimethylcarbamoyloxyphenyl, thiocarbamoyloxyphenyl, N-trifluoroacetylcarbamoyloxyphenyl, p-methoxybenzyloxyphenyl, di-p-methoxybenzyloxyphenyl, methoxy-p-methoxybenzyloxyphenyl, benzyloxycarbonyloxyphenyl, and p-methoxybenzyloxy-fluorophenyl.

Important groups for Het are oxadiazol, thiadiazol, triazol and tetrazol, optionally substituted by methyl, ethyl, hydroxymethyl, hydroxyethyl, carboxymethyl, and carboxyethyl optionally protected in the forms of p-methoxybenzyl, diphenylmethyl, or indanyl esters.

Important groups for $COB^1$ and $COB^2$ are carboxy, diphenylmethoxycarbonyl, p-methoxybenzyloxycarbonyl, indanyloxycarbonyl, phenacyloxycarbonyl, benzyloxycarbonyl, trichloroethoxycarbonyl, phthalidyloxycarbonyl, pivaloyloxymethyloxycarbonyl, t-butoxycarbonyl, trimethylsilyloxycarbonyl, or pharmaceutically acceptable salts thereof, especially the sodium, potassium, magnesium, or calcium salts.

Representatives of Compounds (I) include those having the following groups in said formula:

(1) Ar is p-hydroxyphenyl, p-acetoxyphenyl, p-carbamoyloxyphenyl, 3,4-dihydroxyphenyl, 3-methoxy-4-hydroxyphenyl, 2-fluoro-4-hydroxyphenyl, 2-thienyl, or 3-thienyl; Het is 1-methyl-1H-tetrazol-5-yl; and $COB^1$ and $COB^2$ are carboxy.

(2) Ar is p-hydroxyphenyl; Het is 1,2,3-triazol-4-yl or 2-carboxymethyl-1,3,4-thiadiazol-5-yl; and $COB^1$ and $COB^2$ are carboxy.

(3) Ar is 3-thienyl or p-hydroxyphenyl; Het is 1-methyl-1H-tetrazol-5-yl; $COB^1$ is 5-indanyloxycarbonyl; and $COB^2$ is carboxyl.

(4) Ar is 3,4-dihydroxyphenyl, and Het is 2-methyl-1,3,4-thiadiazol-5-yl; and $COB^1$ and $COB^2$ are carboxy;

Ar is 3-chloro-4-hydroxphenyl, Het is 1,3,4-thiadiazol-5-yl, $COB^1$ and $COB^2$ are carboxys;

Ar is butyryloxyphenyl, Het is 1,3,4-oxadiazol-5-yl, and $COB^1$ and $COB^2$ are carboxys;

Ar is p-thiocarbamoyloxyphenyl, Het is 1,2,3-triazol-4-yl, and $COB^1$ and $COB^2$ are carboxys;

Ar is p-dimethylcarbamoyloxyphenyl, Het is 1-methyl-1H-tetrazol-5-yl, and $COB^1$ and $COB^2$ are carboxys;

Ar is 3-methyl-4-benzoyloxyphenyl, Het is 1-methyl-1,3,4-thiadiazol-5-yl, and $COB^1$ and $COB^2$ are carboxys;

Ar is 3,4-dihydroxyphenyl, Het is 1-methyl-1H-tetrazol-5-yl, and $COB^1$ and $COB^2$ are carboxys;

Ar is 3,4-dicarbamoyloxyphenyl, Het is 1-methyl-1H-tetrazol-5-yl, and $COB^1$ and $COB^2$ are carboxys;

Ar is 3-methoxy-4-hydroxyphenyl, Het is 1-methyl-1H-tetrazol-5-yl, and $COB^1$ and $COB^2$ are carboxys;

Ar is 3-methoxy-4-acetoxyphenyl, Het is 1-methyl-1H-tetrazol-5-yl, and $COB^1$ and $COB^2$ are carboxys;

Ar is 3-methoxy-4-carbamoyloxyphenyl, Het is 1-methyl-1H-tetrazol-5-yl, $COB^1$ is phthalidyloxycarbonyl, and $COB^2$ is carboxy;

Ar is p-acetoxyphenyl, Het is 1-methyl-1H-tetrazol-5-yl, $COB^1$ is 5-indanyloxycarbonyl, and $COB^2$ is carboxy;

Ar is 3,5-dichloro-4-hydroxphenyl, Het is 1,3,4-thiadiazol-5-yl, $COB^1$ is pivaloyloxymethoxycarbonyl, and $COB^2$ is carboxy;

Ar is 3,4,5-trihydroxyphenyl, Het is 2-hydroxymethyl-1,3,4-thiadiazol-5-yl, and $COB^1$ and $COB^2$ are carboxys;

Ar is p-hydroxyphenyl, Het is tetrazol-5-yl, and $COB^1$ and $COB^2$ are carboxys;

Ar is p-acetoxyphenyl, Het is 1,2,3-triazol-4-yl, and $COB^1$ and $COB^2$ are carboxys; and Ar is p-carbamoyloxyphenyl, Het is 1,2,3-triazol-4-yl, and $COB^1$ and $COB^2$ are carboxys.

Pharmaceutically acceptable salts (e.g. sodium, potassium, calcium, or magnesium salts) of the above compounds (1) through (4) are also important for use as an active ingredient in antibacterial drugs.

Other types of important compounds are derivatives of the specific compounds referred to above (1) through (4) in which a phenolic hydroxy group is protected in the form of a p-methoxybenzyl ether or benzyloxycarbonic acid ester, $COB^1$ and $COB^2$ as carboxys are protected in the form of a diphenylmethyl ester, p-methoxybenzyl ester, indanyl ester, phenacyl ester, benzyl ester, 2,2,2-trichloroethyl ester, phthalidyl ester, pivaloyloxymethyl ester, trimethylsilyl ester, or t-butyl ester. These compounds are conveniently used for preparing carboxylic acid and phenolic compounds as an intermediate, as are explained in detail in the Examples. These groups are selected only for the present convenience of experiments. The structure is widely variable so far as available for protection, because the specific structure is no requisite for the object.

II. PRIOR ARTS

Compounds represented by formula I, but wherein Ar is unsubstituted phenyl are described in Japanese Patent Application OPI (Open-to-public Inspection) No. 50-71693 filed by Eli Lilly & Co.; and Compounds represented by formula I, but lacking the 7α-methoxy are described in Japanese Patent Application OPI No. 50-142592 (Beecham Group Limited) and No. 51-1489 (Recherche et Industrie Therapeutique). No description is found this prior art concerning in a compound in which the 7α-position is other than hydrogen.

III. EFFECTS

Compounds I are superior than the corresponding 7α-unsubstituted ones in the following merits:

(i) enhanced antibacterial activity against gram negative bacteria in vitro and in vivo;

(ii) Diminished lowering of antibacterial potency against β-lactamase producing bacteria;

(iii) Enhanced antipseudomonal activity i.e. ½ of carbenicillin in (7αH) analogs is enhanced from about 4 to 10 times; and (iv) Slightly improved stability in human serum.

Compounds I are superior than the corresponding 7β-unsubstituted phenyl-malonamido derivatives in the following merits:

(i) Enhanced activity against pseudomonal bacteria in vitro and in vivo;

(ii) High blood level; and (iii) High stability in human serum.

Free acids are suitable for parenteral administration together with basic aqueous solution for injection.

IV. PRODUCTION

Compounds I can be produced by the following methods:

(1) 7β-amino-7α-methoxy-3-heterocyclic thiomethyl-3-cephem-4-carboxylic acids or their derivatives at the carboxy and optionally activated at the amino in the forms of e.g. isocyano, isocyanato, 1-haloalkylideneamino, 1-alkoxyalkylideneamino, or silylamino are acylated with an arylmalonic acid of the formula:

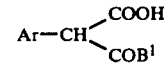

(wherein Ar and $COB^1$ are as defined above) or its reactive derivatives (e.g. a free acid, acid halide, aci anhydride, reactive ester, reactive amide, or ketene), if required in the presence of a catalyzer (e.g. a base, molecular sieve, carbodiimide, epoxide, or enzyme);

(2) 7β-arylmalonamido-7α-methoxycephalosporanic acid or its salt is treated with a mercaptan derivative of the formula:

(wherein Het is as defined above) e.g. in an aqueous solvent under heating or in a non aqueous solvent;

(3) To a 7β-arylmalonamido-3-heterocyclic thiomethyl-3-cephem-4-carboxylic acid or its derivative at the carboxy is introduced a methoxy at the 7α-position, e.g. by the action of lithium methoxide and t-butyl hypohalite in methanol;

(4) reduction of a 7β-arylmalonamido-7α-methoxy-3-heterocyclic thiomethyl-3-cephem-4-carboxylic acid 1-oxide with e.g. triphenylphosphine, stannous chloride, or phosphorus trihalide in the presence of acetyl chloride;

(5) deprotection of Compounds I, where the carboxy group(s) being protected, by a suitable method for the protecting group such as hydrolysis, reduction, solvolysis, photochemical reaction, etc.;

(6) salt formation of Compounds I having carboxy with a base or base salt having a desired cation;

(7) removal of R of compound I where R is a protecting group for phenolic hydroxy to give Compound I where R is hydrogen;

(8) acylation of Compound I where R is a hydrogen to give Compound I where R is acyl; and (9) other methods conventional in the chemistry of penicillins and cephalosporins.

V. STARTING MATERIALS

The starting materials for the said productions are known substances or Compound of this invention, or those preparable by known methods from said substances.

VI. PRODUCTS

Products of each reaction can be obtained by removing unreacted starting materials, reagents, solents, etc. by conventional extraction, washing, concentration, drying, etc., and purified by conventional recrystallization, reprecipitation, chromatography, etc.

Compounds I are strong antibacterials against gram positive and negative bacteria, and useful as antibacterial agents. For example, treatment or prevention of bacterial infections of man can be done by intravenous administration of 10 mg to 2 g a day. It is possible to conventionally produce enteral or topical drugs by adding a suitable additive thereto. Further, Compounds I are useful as intermediates for producing other antibacterials.

The compounds (I) are valuable antibacterials against various gram positive and negative bacteria, and useful as drugs for human and veterinary uses. They can be used for treating or preventing infections caused by gram positive bacteria (e.g. *Staphylococcus aureus, Streptococcus pyogenes, Bacillus subtilis, Bacillus cereus, Diplococcus pneumoniae*) and gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella typhi, Serratia marcesens*) and some are moderately active even against Pseudomonas species. The compounds can be used also as disinfectants for preventing bacterial growth of perishables, feedstuffs, or hygenical materials.

The compounds (I) can be used in wide variety of oral or parenteral dosage forms solely or in admixture with other coating substances. The pharmaceutical compositions may be a mixture of 0.01 to 99% of Compound (I) with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injections, ointments, dispersions, inhalant, suspensions, solutions, emulsions, styrups, or elixirs. They may be flavored and colored, and the tablets, granules, and capsules may be coated. All of the known diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrups, sorbitol, polyvinylpyrrolidone); disintegrators (e.g. starch, agar, carbonates, sodium laurylsulfate); lubricants (e.g. stearic acid, talc, paraffin, boric acid, silica, sodium benzoate, polyethylene glycol, cacao oil, magnesium stearate, emulsifying agents (e.g. lecithin, sorbitan monooleate, acacia); suspending agents (e.g. sorbitol, methyl cellulose, glucose, or sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, analgesics, dispersing agents, wetting agents, antioxidants, and the like can be used if the agents do not exert an adverse effect on the compounds, according to the methods conventional in the art.

Compounds (I) having one or more carboxylic acid salt groups are soluble in water, and are conveniently used as as solution for intravenous, intramuscular, or subcutaneous injection according to a conventional method. The compounds can be dissolved in aqueous or oily solvents for injection to give a solution in an ampoule, but generally, more prolonged storage is possible by making a vial preparation containing crystals, powder, microcrystals, or lyophilizate of Compound (I), and dissolving or suspending the drug before use with the said solvents for injection. The preparation may contain preferably said preservative. The vial preparation or injection can be given to a patient at a daily dose of e.g. 0.1 to 100 mg/kg body weight depending on the infected bacteria, condition of the patient, and interval of the administration.

Compounds (I), especially those having $COB^1$ being a pharmaceutically acceptable ester grouping (e.g. indanyl, acetoxymethyl, pivaloyloxymethyl, ethoxycarbonyloxymethyl, phenacyl, phthalidyl, phenyl, tolyl, xylyl, methoxyphenyl esters), can be adsorbed through the digestive organ to some extent, and can be administered to human or veterinary subjects as powder, tablets, granules, capsules, dry syrup, emulsions, solution, suspension and like oral preparations. These may be pure compounds or a composition comprising Compounds (I) and said pharmaceutical carriers. The preparation can be made according to the methods conventional in the art, and can be administered to a patient at a daily dose of e.g. 1 to 50 mg/kg body weight depending on the condition of patient and the disease.

Further, Compounds (I) can be used as suppositories, ointments for topical or ocular use, powders for topical use, and like preparations preparable according to methods well known to those skilled in the art. The external preparation can contain 0.01 to 99% of the Compound (I) together with a necessary amount of pharmaceutical carrier given above. A necessary amount e.g. 1 µg to 1 mg of the preparation can be applied to the infected part.

This invention also provides a method for treating or preventing human or veterinary bacterial infections by administering to the human or animal subject an effective amount of Compound (I) at a daily dose of e.g. 0.5 to 10 mg/kg body weight for injection or e.g. 0.5 to 50 mg/kg body weight for oral administration, or 1 µg to 1 mg for topical application at an interval of e.g. 3 to 12 hours.

The method is applicable for treating or preventing some diseases caused by bacteria sensitive to Compounds (I) e.g. pneumonia, bronchitis, pneumonitis, empyema, nasopharyngitis, tonsillitis, rhinitis, dermatitis, pustulosis, ulceration, abscess, wound and soft tissue infections, ear infections, osteomyelitis, septicemia, gastroenteritis, enteritis, urinary tract infections, and pyelonephritis when caused by bacteria sensitive to Compound (I).

Preferably the Compounds (I) are given to a patient in the forms of pharmaceutical preparations e.g. powder, dry syrup, tablets, troches, granules, capsules, pills, suppositories, injections, ointments, dispersions, inhalant, suspensions, solutions, emulsions, syrups, and elixirs. They may be in a unit dosage form e.g. tablets, troches, capsules, injections, vials, granules or powder in a separate container or package.

The following examples explain some details of the compounds and production method of this invention, but are not intended to limit the scope thereof.

EXAMPLE 1 (Preparation of starting materials)

A solution of diphenylmethyl 7β-amino-3-(1-methyl-1H-tetrazol-5-yl)thiomethyl-3-cephem-4-carboxylate (9.89 g) and 3,5-di-t-butyl-4-hydroxybenzaldehyde (5.62 g) in a mixture of benzene (160 ml) and dichloromethane (40 ml) is refluxed for 1 hour in the presence of a molecular sieve to give a solution of diphenylmethyl 7β-(3,5-di-t-butyl-4-hydroxy-benzylidene)amino-3-(1-methyl-1H-tetrazol-5-yl)thiomethyl-3-cephem-4-carboxylate.

TLC: Rf 0.59 (Benzene+acetic acid (4:1)/Precoated silica gel plate of E. Merck A.G.)

The solution cooled at $-10°$ to $-15°$ C. is stirred at $-10°$ to $-15°$ C. for 30 minutes and at room temperature for 30 minutes in the presence of dichloromethane (20 ml), magnesium sulfate (5 g), and nickel peroxide (11.0 g) to form diphenylmethyl 7β-(3,5-di-t-butyl-4-oxocyclohexa-2,5-dienylidene)amino-3-(1-methyl-1H-tetrazol-5-yl)thiomethyl-3-cephem-4-carboxylate in the mixture.

To the mixture is added methanol (100 ml). After keeping at room temperature overnight, the mixture is evaporated under reduced pressure to give diphenylmethyl 7α-methoxy-7β-(3,5-di-t-butyl-4-hydroxybenzylidene)amino-3-(1-methyl-1H-tetrazol-5-yl)thiomethyl-3-cephem-4-carboxylate.

IR: $\nu_{max}^{CHCl_3}$ 3620, 1774, 1720 cm$^{-1}$.

NMR: $\delta^{CDCl_3}$ 1.43s18H, 3.52s5H, 3.70s3H, (4.08d+4.38d)ABq(14 Hz)2H.

TLC: Rf 0.63 (Benzene+ethyl acetate (4:1)/Precoated silica gel plate of E. Merck A.G.).

Diphenylmethyl 7α-methoxy-7β-(3,5-di-t-butyl-4-hydroxybenzylidene)amino-3-(1-methyl-1H-tetrazol-5-yl)thiomethyl-3-cephem-4-carboxylate is dissolved in a mixture of tetrahydrofuran (50 ml) and methanol (200 ml) and stirred at room temperature for 1 hour in the presence of Girard's reagent T. The reaction mixture is concentrated, dissolved in ethyl acetate and water, shaken, and the organic layer separated. The layer is washed with saline, dried over sodium sulfate, and concentrated in vacuo. The residue is chromatographed on silica gel (200 g) containing 10% water, eluted with a mixture of benzene and ethyl acetate (2:1), and crystallized from methanol to yield diphenylmethyl 7α-methoxy-7β-amino-3-(1-methyl-1H-tetrazol-5-yl)thiomethyl-3-cephem-4-carboxylate (5.21 g).

Over-all yield: 49.7%.

m.p. 120°–124° C.

IR: $\nu_{max}^{CHCl_3}$ 3400, 3330, 1772, 1717 cm$^{-1}$.

NMR: $\delta^{CDCl_3}$ 2.23s2H, 3.48s3H, 3.60s2H, 3.80s3H, (4.20d+4.48d)ABq (14 Hz)2H, 4.82s1H, 6.92s1H.

EXAMPLE 2 (Amide formation)

To a solution of α-diphenylmethoxycarbonyl-α-p-(p-methoxybenzyloxy)phenylacetic acid (742 mg) in dichloromethane (5 ml) are added triethylamine (167 μl) and oxalyl chloride (102 μl), and the mixture is stirred at 0° C. for 15 minutes to give a solution of α-diphenylmethoxycarbonyl-α-p-(p-methoxybenzyloxy)phenylacetyl chloride in dichloromethane.

To a solution of diphenylmethyl 7α-methoxy-7β-amino-3-(1-methyl-1H-tetrazol-5-yl)thiomethyl-3-cephem-4-carboxylate (525 mg) in dichloromethane (5 ml) are added said solution of the acid chloride in dichloromethane and pyridine (97 μl) at 0° C., and the mixture is stirred at 0° C. for 30 minutes. The reaction mixture is diluted with ethyl acetate, washed with diluted hydrochloric acid, water, aqueous sodium hydrogen carbonate, and water, dried over sodium sulfate, and concentrated under reduced pressure. The residue is chromatographed over silica gel (100 g) containing 10% water and eluted with a mixture of benzene and ethyl acetate (4:1) to afford diphenylmethyl 7α-methoxy-7β-[α-diphenylmethoxycarbonyl-α-p-(p-methoxybenzyloxy)-phenylacetamido]-3-(1-methyl-1H-tetrazol-5-yl)thiomethyl-3-cephem-4-carboxylate (906 mg) in 91.6% yield. Colorless foam.

IR: $\nu_{max}^{CHCl_3}$ 3400, 3320, 1787, 1732, 1700 cm$^{-1}$.

NMR: $\delta^{CDCl_3}$ 3.40s2H, 3.43s3H, 3.78s3H, 3.81s3H, (4.20+4.50)ABq (14 Hz)2H, 4.75s1H, 5.00s3H.

Similarly, the following compounds are prepared:

(1) Diphenylmethyl 7α-methoxy-7β-amino-3-(1-methyl-1H-tetrazol-5-yl)thiomethyl-3-cephem-4-carboxylate (525 mg) and α-p-hydroxyphenyl-α-diphenylmethoxycarbonylacetyl chloride [prepared by reacting α-diphenylmethoxycarbonyl-α-p-hydroxyphenylacetic acid (1.10 g), triethylamine (305 μl), and oxalyl chloride (188 μl) in methylene chloride (6 ml)] are permitted to react in dichloromethane (6 ml) at 0° C. for 30 minutes in the presence of pyridine (177 μl) to give diphenylmethyl 7α-methoxy-7β-(α-diphenylmethoxycarbonyl-α-p-hydroxyphenylacetamido)-3-(1-methyl-1H-tetrazol-5-yl)thiomethyl-3-cephem-4-carboxylate (487.3 mg) in 56.1% yield. Colorless foam.

IR: $\nu_{max}^{CHCl_3}$ 3580, 3400, 3320, 1785, 1725, 1700(sh) cm$^{-1}$.

NMR: $\delta^{CDCl_3}$ 3.32s2H, 3.42s3H, 3.43s3H, 3.75s3H, (4.18+4.45)ABq (14 Hz)2H, 4.73s1H, 5.00s1H.

(2) Diphenylmethyl 7α-methoxy-7β-amino-3-(1-methyl-1H-tetrazol-5-yl)thiomethyl-3-cephem-4-carboxylate (105 mg) and α-diphenylmethoxycarbonyl-α-(3-thienyl)acetyl chloride in methylene chloride [prepared by stirring α-diphenylmethoxycarbonyl-α-(3-thienyl)acetic acid (141 mg), triethylamine (42 μl) and oxalyl chloride (26 μl) in methylene chloride (1 ml) at 0° C. for 15 minutes] in methylene chloride (2 ml) are permitted to react at 0° C. for 15 minutes in the presence of pyridine (24 μl) to give diphenylmethyl 7α-methoxy-7β-[α-diphenylmethoxycarbonyl-α-(3-thienyl)acetamido]-3-(1-methyl-1H-tetrazol-5-yl)thiomethyl-3-cephem-4-carboxylate (132 mg) in 77% yield. Colorless foam.

IR: $\nu_{max}^{CHCl_3}$ 1790, 1730, 1700 cm$^{-1}$.

NMR: $\delta^{CDCl_3}$ 6.95s2H, 5.00s1H, 4.93s1H, 4.50d(13 Hz)1H, 4.19d(13 Hz)1H, 3.77s3H, 3.40s5H.

(3) Diphenylmethyl 7α-methoxy-7β-amino-3-(1-methyl-1H-tetrazol-5-yl)thiomethyl-3-cephem-4-carboxylate (105 mg) and α-diphenylmethoxycarbonyl-α-(2-thienyl)acetyl chloride [prepared by reacting α- diphenylmethoxycarbonyl-α-(2-thienyl)acetic acid (141 mg), triethylamine (42 μl), and oxalyl chloride (26 μl) in methylene chloride (1 ml)] are permitted to react in methylene chloride (2 ml) at 0° C. for 30 minutes in the presence of pyridine (24 μl) to give diphenylmethyl 7α-methoxy-7β-[α-diphenylmethoxycarbonyl-α-(2-thienyl)acetamido]-3-(1-methyl-1H-tetrazol-5-yl)-thiomethyl-3-cephem-4-carboxylate (131 mg) in 77% yield. Colorless foam.

IR: $\nu_{max}^{CHCl_3}$ 1790, 1730, 1705 cm$^{-1}$.

NMR: $\delta^{CDCl_3}$ 6.95s2H, 5.10s1H, 4.97s1H, 4.50d(13 Hz)1H, 4.17d(13 Hz)1H, 3.75s3H, 3.40s3H, 3.37s2H.

(4) Diphenylmethyl 7β-[α-(p-methoxybenzyloxyphenyl)-α-(p-methoxybenzyloxycarbonyl)acetamido]-7α-methoxy-3-(2-carboxymethyl-1,3,4-thiadiazol-5-yl)thiomethyl-3-cephem-4-carboxylate (300 mg) from 475 mg of diphenylmethyl 7β-amino-7α-methoxy-3-(2-diphenylmethoxycarbonyl-1,3,4-thiadiazol-5-yl)thiomethyl-3-cephem-4-carboxylate methylene chloride (15 ml), pyridine (78 mg) and α-(p-methoxybenzyloxyphenyl)-α-(p-methoxybenzyloxycarbonyl)acetyl chloride prepared from 633 mg of the corresponding acid.

IR: $\nu_{max}^{CHCl_3}$ 1790, 1730, 1690sh cm$^{-1}$.

NMR: $\delta^{CDCl_3}$ (3.43s+3.48s)5H, 3.83s6H, 4.22s2H, 4.50ABq2H, 4.65s1H, (5.00s+5.03s+5.17s)5H, 6.8–7.6 m.

(5) Diphenylmethyl 7β-[α-diphenylmethoxycarbonyl-α-p-(p-methoxybenzyloxyphenyl)acetamido]-7α-methoxy-3-(1,2,3-triazol-4-yl)thiomethyl-3-cephem-4-carboxylate (8.1 mg) from 61.3 mg of diphenylmethyl 7β-amino-7α-methoxy-3-(1,2,3-triazol-4-yl)thiomethyl-3-cephem-4-carboxylate, 14.5 μl of pyridine, and 116 mg of α-diphenylmethoxycarbonyl-α-(p-methoxybenzyloxyphenyl)acetyl chloride.

IR: $\nu_{max}^{CHCl_3}$ 1780, 1721, 1685 cm$^{-1}$.

NMR: $\delta^{CDCl_3}$ 3.20s3H, 3.43s3H, 3.83s3H, (3.98+4.10)2H, (4.63+4.77) 1H, 4.98s1H, 3.03(2H).

(6) Diphenylmethyl 7β-[α-(3,4-di-p-methoxybenzyloxyphenyl)-α-diphenylmethoxycarbonylacetamido]-7α-methoxy-3-(1-methyl-1H-tetrazol-5-yl)thiomethyl-3-cephem-4-carboxylate (850 mg) from 500 mg of diphenylmethyl 7β-amino-7α-methoxy-3-(1-methyl-1H-tetrazol-5-yl)thiomethyl-3-cephem-4-carboxylate, 25 ml of methylene chloride, 115 μl of pyridine and α-(3,4-di-p-methoxybenzyloxyphenyl)-α-diphenylmethoxycarbonylacetyl chloride prepared from 1.2 g of the corresponding acid.

IR: $\nu_{max}^{CHCl_3}$ 1795, 1730, 1710 cm$^{-1}$.

NMR: $\delta^{CDCl_3}$ (3.33brs+3.40brs)5H, (3.73s+3.77s)9H, 4.33ABq(14 Hz) 2H, 4.67s1H, 4.87s2H, 4.97s1H, 5.03s2H, 6.7–7.6 m.

(7) Diphenylmethyl 7β-[α-(4-p-methoxybenzyloxy-3-methoxyphenyl-α-p-methoxybenzyloxycarbonylacetamido]-7α-methoxy-3-(1-methyl-1H-tetrazol-5-yl)thiomethyl-3-cephem-4-carboxylate.

IR: $\nu_{max}^{CHCl_3}$ 1795, 1725, 1705sh cm$^{-1}$.

NMR: $\delta^{CDCl_3}$ (3.40brs+3.38brs)5H, 3.77s12H, 4.33ABq(14 Hz)2H, 4.57s1H, 4.97s1H, 5.02s2H, 5.10s2H, 6.7–7.6 m.

(8) Diphenylmethyl 7β-[α-(4-p-methoxybenzyloxyphenyl)-α-p-methoxybenzyloxycarbonylacetamido]-7α-methoxy-3-(1-methyl-1H-tetrazol-5-yl)thiomethyl-3-cephem-4-carboxylate in 75% yield.

IR: $\nu_{max}^{CHCl_3}$ 1787, 1732, 1700 cm$^{-1}$.

NMR: $\delta^{CDCl_3}$ 3.38brs2H. 3.40s3H. 3.50s3H, 3.52s3H, 3.57s3H, [4.17d(12 Hz)1H,+4.50d(12 Hz)1H]ABq, 4.67brs1H, 4.92s2H, 4.97s1H, 5.10s2H.

(9) Diphenylmethyl 7β-[α-(4-p-methoxybenzyloxy-2-fluorophenyl)-α-diphenylmethoxycarbonylacetamido]-7α-methoxy-3-(1-methyl-1H-tetrazol-5-yl)thiomethyl-3-cephem-4-carboxylate (200 mg) from 7β-amino-7α-methoxy-3-(1-methyl-1H-tetrazol-5-yl)thiomethyl-3-cephem-4-carboxylic acid diphenylmethyl ester (157 mg), methylene chloride (4 ml), pyridine 50 μl, and α-4-(p-methoxybenzyl)oxy-2-fluorophenyl-α-diphenylmethoxycarbonylacetyl chloride prepared from 300 mg of the corresponding acid, 62 μl of triethylamine, and 38 μl of oxalyl chloride in methylene chloride.

NMR: $\delta^{CDCl_3}$ 3.47s5H, 3.70s3H, 3.77s6H, 4.30ABq(14;20 Hz)2H, 4.93s2H, 5.00s2H, 6.5–7.7 m27H.

(10) Diphenylmethyl 7β-[α-(3-thienyl)-α-(5-indanyl)oxycarbonylacetamido]-7α-methoxy-3-(1-methyl-1H-tetrazol-5-yl)thiomethyl-3-cephem-4-carboxylate.

IR: $\nu_{max}^{CHCl_3}$ 3400, 1788, 1739, 1720, 1700 cm$^{-1}$.

(11) Diphenylmethyl 7β-[α-p-hydroxyphenyl-α-(5-indanyl)oxycarbonylacetamido]-7α-methoxy-3-(1-methyl-1H-tetrazol-5-yl)thiomethyl-3-cephem-4-carboxylate.

IR: $\nu_{max}^{CHCl_3}$ 1785, 1735, 1720, 1702 cm$^{-1}$.

EXAMPLE 3 (Carboxylic acids)

To a solution of diphenylmethyl 7α-methoxy-7β-[α-diphenylmethoxycarbonyl-α-p-(p-methoxybenzyloxy)-phenylacetamido]-3-(1-methyl-1H-tetrazol-5-yl)thiomethyl-3-cephem-4-carboxylate (370 mg) in dichloromethane (5 ml) are added anisole (1 ml) and trifluoroacetic acid (1 ml) at 0° C., and the mixture is stirred for 1 hour. The reaction mixture is concentrated under reduced pressure, and residual solid is triturated in ether to give 7α-methoxy-7β-(α-carboxy-α-p-hydroxyphenylacetamido)-3-(1-methyl-1H-tetrazol-5-yl)thiomethyl-3-cephem-4-carboxylic acid (150 mg).

IR: $\nu_{max}^{KBr}$ 1775, 1725 cm$^{-1}$.
UV: $\lambda_{max}^{CH_3OH}$ 276.5 nm (ε=9,700).
$[\alpha]_D^{23}$ +70.6±1.1 (1.021%, CH$_3$OH).

The following free carboxylic acids are preparable from the corresponding diphenylmethyl esters in procedures similar to the above examples.

(1) 7α-methoxy-7β-(α-carboxy-α-p-acetoxyphenylacetamido)-3-(1-methyl-1H-tetrazol-5-yl)thiomethyl-3-cephem-4-carboxylic acid in 96.2% yield as colorless powder.
m.p. 116°–122° C.
IR: $\nu_{max}^{KBr}$ 1765 cm$^{-1}$.
UV: $\lambda_{max}^{CH_3OH}$ 272 nm (ε=8,000).
$[\alpha]_D^{23}$ +80.1±1.1° (1.056%, CH$_3$OH).

(2) 7α-methoxy-7β-(α-carboxy-α-p-carbamoyloxyphenylacetamido)-3-(1-methyl-1H-tetrazol-5-yl)thiomethyl-3-cephem-4-carboxylic acid as colorless powder.
m.p. 138°–140° C.
IR: $\nu_{max}^{KBr}$ 1778, 1729, 1710(sh) cm$^{-1}$.

(3) 7α-methoxy-7β-[α-carboxy-α-(3-thienyl)acetamido]-3-(1-methyl-1H-tetrazol-5-yl)thiomethyl-3-cephem-4-carboxylic acid as colorless powder.
m.p. 110°–118° C.
IR: $\nu_{max}^{KBr}$ 1777, 1725, 1700 cm$^{-1}$.
UV: $\lambda_{max}^{CH_3OH}$ 275 nm (ε=7,570).
$[\alpha]_D^{25}$ +72.8±2.8° (0.401%, CH$_3$OH).

(4) 7α-methoxy-7β-[α-carbonyl-α-(2-thienyl)acetamido]-3-(1-methyl-1H-tetrazol-5-yl)thiomethyl-3-cephem-4-carboxylic acid as colorless powder.
m.p. 109°–119° C.
IR: $\nu_{max}^{KBr}$ 1777, 1725, 1700 cm$^{-1}$.

UV: $\lambda_{max}^{CH3OH}$ 275 nm ($\epsilon$=7,580).

$[\alpha]_D^{25}$+63.6±2.8° (CH$_3$OH, 0.376%).

The same compound is preparable by the reaction of 7β-[α-(2-thienyl)-α-carboxyacetamido]-7α-methoxycephalosporanic acid with sodium 1-methyl-1H-tetrazol-5-ylmercaptide in a buffer solution of PH 6.3 under nitrogen at 50° C. for 6 hours.

(5) 7β-(α-p-hydroxyphenyl-α-carboxyacetamido)-7α-methoxy-3-(1,2,3-triazol-4-yl)thiomethyl-3-cephem-4-carboxylic acid (4.2 mg) as pale yellow powder.

IR: $\nu_{max}^{KBr}$ 1769, 1718, 1683(sh) cm$^{-1}$.

Rf(SiO$_2$-plate Merck A.G.): 0.16[EtOAc+HOAc+H$_2$O(5:1:1:1)].

(6) 7β-(α-p-hydroxyphenyl-α-carboxyacetamido)-7α-methoxy-3-(2-carboxymethyl-1,3,4-thiadiazol-5-yl)thiomethyl-3-cephem-4-carboxylic acid (105 mg).

IR: $\nu_{max}^{Nujol}$ 1770, 1720, 1690 cm$^{-1}$.

(7) 7β-[α-(3,4-dihydroxyphenyl)-α-carboxyacetamido]-7α-methoxy-3-(1-methyl-1H-tetrazol-5-yl)thiomethyl-3-cephem-4-carboxylic acid as pale yellow powder in nearly quantitative yield.

IR: $\nu_{max}^{KBr}$ 1773, 1722, 1692(sh) cm$^{-1}$.

(8) 7β-[α-(4-hydroxy-3-methoxyphenyl)-α-carboxyacetamido]-7α-methoxy-3-(1-methyl-1H-tetrazol-5-yl)thiomethyl-3-cephem-4-carboxylic acid.

IR: $\nu_{max}^{KBr}$ 1775, 1723, 1700(sh) cm$^{-1}$.

(9) 7β-[α-(2-fluoro-4-hydroxyphenyl)-α-carboxyacetamido]-7α-methoxy-3-(1-methyl-1H-tetrazol-5-yl)thiomethyl-3-cephem-4-carboxylic acid (200 mg) from diphenylmethyl 7β-[α-(2-fluoro-4-p-methoxybenzyloxyphenyl)-α-diphenylmethoxycarbonylacetamido]-7α-methoxy-3-(1-methyl-1H-tetrazol-5-yl)thiomethyl-3-cephem-4-carboxylate.

IR: $\nu_{max}^{Nujol}$ 3275, 1770, 1710–1690, 1630 cm$^{-1}$.

NMR: $\delta_{ppm}^{CDCl3+CD3OD}$ (3.47s+3.56s)5H, 3.93s3H, 4.37s2H, 4.83s1H, 5.00s1H, 6.33–7.60ar3H.

(10) 7β-[(3-thienyl)-α-(5-indanyloxycarbonyl)acetamido]-7α-methoxy-3-(1-methyl-1H-tetrazol-5-yl)thiomethyl-3-cephem-4-carboxylic acid from the corresponding mono-diphenylmethyl ester.

IR: $\nu_{max}^{KBr}$ 1775, 1702 cm$^{-1}$.

UV: $\lambda_{max}^{CH3OH}$ 271 nm ($\epsilon$=10500).

(11) 7β-[α-(p-hydroxyphenyl)-α-(5-indanyloxycarbonyl)acetamido]-7α-methoxy-3-(1-methyl-1H-tetrazol-5-yl)thiomethyl-3-cephem-4-carboxylic acid from the corresponding mono-diphenylmethyl ester.

IR: $\nu_{max}^{KBr}$ 1773, 1697 cm$^{-1}$.

UV: $\lambda_{max}^{CH3OH}$ 271 nm ($\epsilon$=11400); 277 nm ($\epsilon$=11400).

EXAMPLE 4 (Acylation of phenol groups)

(1) To a solution of diphenylmethyl 7α-methoxy-7β-(α-diphenylmethoxycarbonyl-α-p-hydroxyphenylacetamido)-3-(1-methyl-1H-tetrazol-5-yl)thiomethyl-3-cephem-4-carboxylate (100 mg) in methylene chloride (1 ml) are added pyridine (50 μl) and acetic anhydride (100 μl), and the mixture is kept at 0° C. overnight. The reaction mixture is diluted with ethyl acetate, washed with water, dried over sodium sulfate, and evaporated under reduced pressure. The residue is chromatographed over silica gel containing 10% water, and eluted with a mixture of benzene and ethyl acetate (9:1) to give diphenylmethyl 7α-methoxy-7β-(α-diphenylmethoxycarbonyl-α-p-acetoxyphenylacetamido)-3-(1-methyl-1H-tetrazol-5-yl)thiomethyl-3-cephem-4-carboxylate (93 mg) as colorless foam in 89.4% yield.

IR: $\nu_{max}^{CHCl3}$ 3415, 3325, 1785, 1760(sh), 1728, 1700(sh) cm$^{-1}$.

NMR: $\delta^{CDCl3}$ 2.28s3H, 3.37s2H, 3.42s3H, 3.80s3H, 4.18+4.53ABq(14 Hz) 2H, 4.82s1H, 5.00s1H.

The same compounds can be prepared by reducing diphenylmethyl 7β-(α-p-acetoxyphenyl-α-diphenylmethoxycarbonylacetamido)-7α-methoxy-3-(1-methyl-1H-tetrazol-5-yl)thiomethyl-3-cephem-4-carboxylate 1-oxide with stannous chloride in dimethylformamide in the presence of acetyl chloride.

(2) To a solution of diphenylmethyl 7α-methoxy-7β-(α-diphenylmethoxycarbonyl-α-p-hydroxyphenylacetamido)-3-(1-methyl-1H-tetrazol-5-yl)thiomethyl-3-cephem-4-carboxylate (260 mg) in methylene chloride (4 ml) is added trichloroacetyl isocyanate (0.3 ml) at −78° C., and the mixture is stirred at −78° C. for 15 minutes and at 0° C. for 30 minutes. The mixture is diluted with water, and extracted with methylene chloride. The organic layer is separated, washed with water, dried over sodium sulfate, and evaporated under reduced pressure. The residue is chromatographed on silica gel (50 g) containing 10% water, and eluted with a mixture of benzene and ethyl acetate (2:1) to give diphenylmethyl 7α-methoxy-7β-(α-diphenylmethoxycarbonyl-α-p-carbamoyloxyphenylacetamido)-3-(1-methyl-1H-tetrazol-5-yl)thiomethyl-3-cephem-4-carboxylate (97.6 mg) as colorless foam in 35.8% yield.

IR: $\nu_{max}^{CHCl3}$ 3540, 3425, 3320, 1780, 1747, 1725, 1700(sh) cm$^{-1}$.

NMR: $\delta^{CDCl3}$ 3.35s2H, 3.40s3H, 3.45s3H, 3.80s3H, 4.19+4.53ABq(13 Hz) 2H, 4.80s1H, 4.98s1H, 5.25s2H.

A by-product, diphenylmethyl 7α-methoxy-7β-[α-diphenylmethoxycarbonyl-α-p-(N-trifluoroacetyl)carbamoyloxyphenylacetamido]-3-(1-methyl-1H-tetrazol-5-yl)thiomethyl-3-cephem-4-carboxylate can be transformed by e.g. hydrolysis or reductive fission to give the said main product.

EXAMPLE 5 (Introduction of methoxy group)

To a solution of diphenylmethyl 7β-(α-p-hydroxyphenyl-α-diphenylmethoxycarbonylacetamido)-3-(1-methyl-1H-tetrazol-5-yl)thiomethyl-3-cephem-4-carboxylate (310 mg) in tetrahydrofuran (15 ml) are added 2 M lithium methoxide in methanol (0.63 ml) and after 1 minute t-butyl hypochlorite (42.6 μl) at −78° C., and the mixture is stirred at −78° C. for 15 minutes. The reaction mixture is mixed with acetic acid (0.3 ml), warmed to room temperature, diluted with ethyl acetate, washed with water, dried over sodium sulfate, and evaporated to dryness under reduced pressure. The residue is chromatographed on silica gel (30 g) containing 10% water and eluted with a mixture of benzene and ethyl acetate (9:1) to give diphenylmethyl 7β-(α-chloro-α-p-hydroxyphenyl-α-diphenylmethoxycarbonylacetamido)-3-(1-methyl-1H-tetrazol-5-yl)thiomethyl-3-cephem-4-carboxylate (206 mg) NMR: $\delta^{CDCl3}$ 5.74dd(4.5;9 Hz)1H, together with the following 7α-methoxy compound.

The product is dissolved in tetrahydrofuran 10 ml, cooled at −78° C., mixed with 2 M lithium methoxide in methanol (0.41 ml) and t-butyl hypochlorite (28 μl) after 1 minute under nitrogen gas, stirred at room temperature for 15 minutes, warmed to room temperature, diluted with ethyl acetate, washed with water, dried, and evaporated to dryness under reduced pressure to give diphenylmethyl 7α-methoxy-7β-(α-chloro-α-diphenylmethoxycarbonyl-α-p-hydroxyphenylacetamido)-3-(1-methyl-1H-tetrazol-5-yl)thiomethyl-3-cephem-4-carboxylate.

NMR: $\delta^{CDCl_3}$ 3.40s3H.

This is reduced with zinc and acetic acid at room temperature to give diphenylmethyl 7β-(α-diphenylmethoxycarbonyl-α-p-hydroxyphenylacetamido)-3-(1-methyl-1H-tetrazol-5-yl)thiomethyl-3-cephem-4-carboxylate.

IR: $\nu_{max}^{CHCl_3}$ 3400, 3320, 1787, 1732, 1700 cm$^{-1}$.

EXAMPLE 6 (Introduction of a heteroaromatic thio group)

To a solution of 235 mg of 7β-[α-(3-thienyl)-α-(5-indanyloxycarbonyl)acetamido]-7α-methoxy-3-acetoxymethyl-3-cephem-4-carboxylic acid in 3 ml of dichloromethane is added 70 mg of 5-mercapto-1-methyltetrazol, and the mixture refluxed for 30 minutes under nitrogen gas. Then, additional 23 mg of 5-mercapto-1-methyltetrazol is added, and the mixture is refluxed for 3.5 hours to form 7β-[α-(3-thienyl)-α-(5-indanyloxycarbonyl)acetamido]-7α-methoxy-3-(1-methyl-1H-tetrazol-5-yl)thiomethyl-3-cephem-4-carboxylic acid. After cooling, 200 mg of diphenyldiazomethane dissolved in 1 ml of methylene chloride is added to the reaction mixture, stirred at 0° C. for 15 minutes to give 145 mg of the corresponding diphenylmethyl ester as pale yellow foam in 44.8% yield.

IR: $\nu_{max}^{CHCl_3}$ 3400, 1788, 1739, 1720, 1700 cm$^{-1}$.

NMR: $\delta^{CDCl_3}$ 5.05s1H, 5.01s1H, 4.50d(14 Hz)1H, 4.18d(14 Hz)1H, 3.75s3H, 3.48brs5H, 2.87t(7 Hz)4H, 2.00m2H.

Similarly prepared is 118 mg of diphenylmethyl 7β-[α-p-hydroxyphenyl-α-(5-indanyloxycarbonyl)acetamido]-7α-methoxy-3-(1-methyl-1H-tetrazol-5-yl)thiomethyl-3-cephem-4-carboxylate through the corresponding free acid.

IR: $\nu_{max}^{CHCl_3}$ 1785, 1735, 1720, 1702 cm$^{-1}$.

NMR: $\delta_{ppm}^{CDCl_3}$ 2.83t(6 Hz)4H, 3.37brs2H, 3.73s3H, 3.50s3H, 4.35brs2H, 5.00s1H, 4.83s1H.

EXAMPLE 7 (Representative compounds)

According to the methods of the preceding examples, the following compounds are preparable:

(1) 7β-[α-(3,4-dihydroxyphenyl)-α-carboxyacetamido]-7α-methoxy-3-(2-methyl-1,3,4-thiadiazol-5-yl)thiomethyl-3-cephem-4-carboxylic acid and its p-methoxybenzyl ester;

(2) 7β-[α-(3-chloro-4-hydroxyphenyl)-α-carboxyacetamido]-7α-methoxy-3-(1,3,4-thiadiazol-5-yl)thiomethyl-3-cephem-4-carboxylic acid and its phenacyl ester;

(3) 7β-(α-p-butyryloxyphenyl-α-carboxyacetamido)-7α-methoxy-3-(1,3,4-oxadiazol-2-yl)thiomethyl-3-cephem-4-carboxylic acid and its benzyl ester;

(4) 7β-(α-p-thiocarbamoyloxyphenyl-α-carboxyacetamido)-7α-methoxy-3-(1,2,3-triazol-4-yl)thiomethyl-3-cephem-4-carboxylic acid and its 2,2,2-trichloroethyl ester;

(5) 7β-(α-p-dimethylcarbamoyloxyphenyl-α-carboxyacetamido)-7α-methoxy-3-(1-methyl-1H-tetrazol-5-yl)thiomethyl-3-cephem-4-carboxylic acid and its diphenylmethyl ester;

(6) 7β-[α-(4-benzoyloxy-3-methylphenyl)malonamido]-7α-methoxy-3-(2-methyl-1,3,4-thiadiazol-5-yl)thiomethyl-3-cephem-4-carboxylic acid and its phthalidyl ester;

(7) 7β-(α-p-hydroxyphenyl-α-carboxyacetamido)-7α-methoxy-3-(2-carboxymethyl-1,3,4-thiadiazol-5-yl)thiomethyl-3-cephem-4-carboxylic acid and its diphenylmethyl ester;

(8) 7β-[α-(3,4-dihydroxyphenyl)-α-carboxyacetamido]-7α-methoxy-3-(1-methyl-1H-tetrazol-5-yl)thiomethyl-3-cephem-4-carboxylic acid and its diphenylmethyl ester;

(9) 7β-[α-(3,4-biscarbamoyloxyphenyl)-α-carboxyacetamido]-7α-methoxy-3-(1-methyl-1H-tetrazol-5-yl)thiomethyl-3-cephem-4-carboxylic acid and its diphenylmethyl ester;

(10) 7β-[α-(4-hydroxy-3-methoxyphenyl)-α-carboxyacetamido]-7α-methoxy-3-(1-methyl-1H-tetrazol-5-yl)-thiomethyl-3-cephem-4-carboxylic acid and its diphenylmethyl ester;

(11) 7β-[α-(4-acetoxy-3-methoxyphenyl)-α-carboxyacetamido]-7α-methoxy-3-(1-methyl-1H-tetrazol-5-yl)thiomethyl-3-cephem-4-carboxylic acid and its diphenylmethyl ester;

(12) 7β-[α-(4-carbamoyloxy-3-methoxyphenyl)-α-phthalidyloxycarbonylacetamido]-7α-methoxy-3-(1-methyl-1H-tetrazol-5-yl)thiomethyl-3-cephem-4-carboxylic acid and its diphenylmethyl ester;

(13) 7β-[α-p-acetoxyphenyl-α-(5-indanyl)oxycarbonylacetamido]-7α-methoxy-3-(1-methyl-1H-tetrazol-5-yl)thiomethyl-3-cephem-4-carboxylic acid and its diphenylmethyl ester;

(14) 7β-[α-(3,5-dichloro-4-hydroxyphenyl)-α-pivaloyloxymethoxycarbonylacetamido]-7α-(1,3,4-thiadiazol-5-yl)thiomethyl-3-cephem-4-carboxylic acid and its t-butyl ester;

(15) 7β-[α-(3,4,5-trihydroxyphenyl)-α-carboxyacetamido]-7α-methoxy-3-(2-hydroxymethyl-1,3,4-thiadiazol-5-yl)thiomethyl-3-cephem-4-carboxylic acid and its trimethylsilyl ester;

(16) 7β-(α-p-hydroxyphenyl-α-carboxyacetamido)-7α-methoxy-3-(1H-tetrazol-5-yl)thiomethyl-3-cephem-4-carboxylic acid and its diphenylmethyl ester;

(17) 7β-(α-p-acetoxyphenyl-α-carboxyacetamido)-7α-methoxy-3-(1,2,3-triazol-5-yl)thiomethyl-3-cephem-4-carboxylic acid and its diphenylmethyl ester; and

(18) 7β-(α-p-carbamoyloxyphenyl-α-carboxyacetamido)-7α-methoxy-3-(1,2,3-triazol-5-yl)thiomethyl-3-cephem-4-carboxylic acid and its diphenylmethyl ester.

EXAMPLE 8 (Salt formation)

Free acids of Examples 3 and 6 are dissolved in aqueous sodium hydrogen carbonate to give sodium salts, and the evaluated antibacterial potency of the solution shows a minimal inhibitory concentration of less than 1γ/ml against most of the gram negative bacteria.

Minimal inhibitory concentration against pseudomonal bacteria is 50 - 1γ/ml, and that against gram positive bacteria tends to be less active.

EXAMPLE 9 (Pharmaceutical preparations)

(1) Disodium salt of 7β-(α-p-hydroxyphenyl-α-carboxyacetamido)-7α-methoxy-3-(1-methyl-1H-tetrazol-5-yl)thiomethyl-3-cephem-4-carboxylic acid (1 g) in a 5 ml vial is dissolved in 1 ml of water for intravenous injection and infused to an adult patient suffering from urinary tract infection caused by *Klebsiella pneumoniae*.

(2) Powder of 7β-[α-(4-hydroxy-2-fluorophenyl)-α-(5-indanyloxycarbonyl)acetamido]-7α-methoxy-3-(1-methyl-1H-tetrazol-5-yl)thiomethyl-3-cephem-4-carboxylic acid (250 mg) is mixed with potato starch (250 mg), magnesium stearate (10 mg), and talc (10 mg), and the mixed powder is encapsulated in a hard gelatin capsule (500 mg volume). Each one capsule is administered 4 times a day to a patient suffering from an upper respiratory tract infection caused by *Staphylococcus aureus.*

(3) Microcrystals of sodium 7β-[α-(3-thienyl)-α-carboxyacetamido]-7α-methoxy-3-(2-methyl-1,3,4-thiadiazol-5-yl)-thiomethyl-3-cephem-4-carboxylate (1 g) and disodium hydrogen phosphate placed in a vial are dissolved in sterilized water for injection (4 ml) and infused to a post operative patient for prevention of bacterial infection together with nutrient and analgesic drip solution.

The invention being thus described, it will be obvious that the same may be varied in many ways. Such variations are not to be regarded as a departure from the spirit and scope of the invention, and all such modifications are intended to be included within the scope of the following claims.

What we claim is:

1. A compound of the formula:

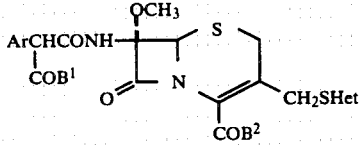

wherein
(1) Ar is p-hydroxyphenyl, Het is 1-methyl-1H-tetrazol-5-yl, and COB¹ and COB² are carboxy or protected carboxy groups;
(2) Ar is p-carbamoyloxyphenyl, Het is 1-methyl-1H-tetrazol-5-yl, and COB¹ and COB² are carboxy or protected carboxy groups;
(3) Ar is 2-fluoro-4-hydroxyphenyl, Het is 1-methyl-1H-tetrazol-5-yl, and COB¹ and COB² are carboxy or protected carboxy groups;
(4) Ar is 2-thienyl, Het is 1-methyl-1H-tetrazol-5-yl, and COB¹ and COB² are carboxy or protected carboxy groups; or
(5) Ar is 3-thienyl, Het is 1-methyl-1-H-tetrazol-5-yl, and COB¹ and COB² are carboxy or protected carboxy groups,
and pharmaceutically acceptable salts thereof.

2. A method for treating or preventing bacterial infection in human or veterinary subjects which comprises administering thereto an effective antibacterial amount of a compound according to claim 1 in a pharmaceutical or veterinary dosage form.

3. An antibacterial pharmaceutical composition comprising an effective antibacterial amount of a compound according to claim 1 and a pharmaceutically acceptable carrier.

4. The compound of claim 1, wherein Ar is p-hydroxyphenyl, Het is 1-methyl-1H-tetrazol-5-yl, and COB¹ and COB² are carboxy or protected carboxy groups.

5. The compound of claim 1, wherein Ar is p-carbamoyloxyphenyl, Het is 1-methyl-1H-tetrazol-5-yl, and COB¹ and COB² are carboxy or protected carboxy groups.

6. The compound of claim 1, wherein Ar is 2-fluoro-4-hydroxyphenyl, Het is 1-methyl-1H-tetrazol-5-yl, and COB¹ and COB² are carboxy or protected carboxy groups.

7. The compound of claim 1, wherein Ar is 2-thienyl, Het is 1-methyl-1H-tetrazol-5-yl, and COB¹ and COB² are carboxy or protected carboxy groups.

8. The compound of claim 1, wherein Ar is 3-thienyl, Het is 1-methyl-1H-tetrazol-5-yl, and COB¹ and COB² are carboxy or protected carboxy groups.

* * * * *